United States Patent
Imran (10) Patent No.: US 9,610,398 B2
(45) Date of Patent: Apr. 4, 2017

(54) IMPLANTABLE SOLID-LIQUID DRUG DELIVERY APPARATUS, FORMULATIONS, AND METHODS OF USE

(71) Applicant: Mir Imran, Los Altos Hills, CA (US)

(72) Inventor: Mir Imran, Los Altos Hills, CA (US)

(73) Assignee: Incube Labs, LLC, San Jose, CA (US)

( * ) Notice: Subject to any disclaimer, the term of this patent is extended or adjusted under 35 U.S.C. 154(b) by 754 days.

(21) Appl. No.: 13/681,261

(22) Filed: Nov. 19, 2012

(65) Prior Publication Data

US 2013/0324969 A1  Dec. 5, 2013

Related U.S. Application Data

(60) Provisional application No. 61/629,666, filed on Nov. 22, 2011.

(51) Int. Cl.
*A61M 5/14* (2006.01)
*A61M 5/142* (2006.01)
*A61M 5/168* (2006.01)

(52) U.S. Cl.
CPC ...... *A61M 5/1409* (2013.01); *A61M 5/14276* (2013.01); *A61M 5/16827* (2013.01); *A61M 2205/0244* (2013.01)

(58) Field of Classification Search
CPC ............ A61M 5/1409; A61M 5/14276; A61M 5/16827; A61M 37/0069

(Continued)

(56) References Cited

U.S. PATENT DOCUMENTS 5,176,641 A  1/1993  Idriss
5,281,197 A *  1/1994  Arias ................ A61M 37/0069
                                                           604/209

(Continued)

FOREIGN PATENT DOCUMENTS

EP  1342481 A1  9/2003
JP  2008508024 A  3/2008

(Continued)

OTHER PUBLICATIONS

International search report and written opinion dated Mar. 11, 2013 for PCT/US2012/066161.

(Continued)

*Primary Examiner* — Theodore Stigell
(74) *Attorney, Agent, or Firm* — Wilson Sonsini Goodrich & Rosati; Joel M. Harris, Esq.

(57) ABSTRACT

Embodiments provide apparatus and methods for delivering liquid form medication within the body wherein the medication is stored in solid form and then mixed with a liquid in an apparatus implanted within the body. One embodiment provides an implantable apparatus for in vivo delivery of medication comprising a housing including a reservoir, a store of solid form medication (SSM) and a pump. An SSM element is added to the reservoir along with fluid to form a medication solution comprising at least one drug. The medication solution is then delivered to a delivery site using a pumping means to pump solution from the reservoir through a delivery member such as catheter to a delivery site. Embodiments of the invention are particularly useful for delivering medication to a patient to treat a medical condition over an extended period of time without requiring the patient to take external medication.

15 Claims, 7 Drawing Sheets

(58) Field of Classification Search
USPC .............................. 604/57, 82, 288.01, 891.1
See application file for complete search history.

(56) References Cited

U.S. PATENT DOCUMENTS

| | | |
|---|---|---|
| 6,416,493 B1 | 7/2002 | Giglio |
| 6,458,118 B1* | 10/2002 | Lent .................. A61M 5/14276 |
| | | 604/288.01 |
| 2005/0234431 A1 | 10/2005 | Williams et al. |
| 2007/0233019 A1 | 10/2007 | Forsell |
| 2007/0255234 A1 | 11/2007 | Haase et al. |
| 2007/0287984 A1* | 12/2007 | Lobl .................. A61M 5/1409 |
| | | 604/416 |
| 2008/0213331 A1 | 9/2008 | Gelfand et al. |

FOREIGN PATENT DOCUMENTS

| | | |
|---|---|---|
| WO | WO 95/04571 A1 | 2/1995 |
| WO | WO 2010/107507 A1 | 9/2010 |

OTHER PUBLICATIONS

European search report and search opinion dated Jul. 28, 2015 for EP Application No. 12851363.7.

\* cited by examiner

IMPLANTABLE SOLID-LIQUID DRUG DELIVERY APPARATUS, FORMULATIONS, AND METHODS OF USE

CROSS-REFERENCE TO RELATED APPLICATIONS

This application claims the benefit of priority U.S. Provisional Patent Application No. 61/629,666 filed Nov. 22, 2011; entitled, "Implantable Solid-Liquid Drug Delivery Apparatus, Formulations and Methods of Use", which is fully incorporated herein by reference for all purposes.

BACKGROUND

Field of the Invention

Embodiments of the invention relate to drug delivery devices and methods of use thereof. More specifically, embodiments of the invention relate to implantable drug delivery devices for the delivery of drugs and other therapeutic agents.

The current trend in many medical treatments requires the delivery of a drug to a specific target site so as to avoid adverse reactions and/or toxicity to other tissue (e.g., in the case of chemotherapeutic agents for the treatment of cancer), as well as more precisely controlling the timing and amount of drug delivered to that site. In many cases, this can entail the use of an implantable drug pump. However, due to their size and power requirements the current available pumps do not lend themselves to all medical applications, particularly for delivery of drugs where very precisely controlled doses of the drug can be required. Also current devices can require frequent replenishment of the drug due to limited reservoir size and/or limited shelf life of the drug. Thus, there is a need for improved implantable drug delivery devices and associated methods for in vivo drug delivery.

BRIEF SUMMARY

Embodiments of the invention provide apparatus, systems, formulations and methods for delivering medication to various locations in the body of a human patient or mammal. The present invention is directed to the delivery of liquid medication to a patient. Many of the contemplated embodiments encompass the delivery of the liquid medication via an implantable drug apparatus and methods of use thereof. The present invention provides an implantable drug delivery apparatus for delivering a liquid medication to a delivery site such as blood vessel of a patient, though other delivery sites are also contemplated. In exemplary embodiments, the implantable apparatus comprises an implantable housing having an external wall and an internal space. Within the internal space is a mixing chamber, wherein the mixing chamber (also referred to as a reservoir) is configured to receive transcutaneous transfers of a liquid. A plurality of solid medication doses is also located in the internal space. The mixing chamber is configured to receive individual medication doses, wherein the individual solid medication dosages dissolve or become suspended in the liquid to form the liquid medication. The implantable apparatus for delivering the liquid medication further comprises a catheter configured to receive the liquid medication from the mixing chamber and to deliver the liquid medication to the blood vessel or other delivery site.

In preferred embodiments, the mixing chamber has an access port through the external wall of the housing to permit injection using needle and syringe. In yet another aspect, preferred embodiments of the implantable apparatus further comprise a transfer mechanism for advancing individual solid medication doses into the mixing chamber. In yet another aspect, the transfer mechanism may advances the individual solid medication dose through a resealable septum such as a split membrane in a side of the mixing chamber. In some embodiments, the individual solid medication doses are carried in a carousel which is incremented to move individual doses adjacent to the split membrane.

In yet another preferred embodiment, the implantable apparatus may further comprise an intermediate chamber between the mixing chamber and the catheter. Preferred embodiments may further comprise a pump for delivering liquid medication doses through the catheter to the delivery site. In yet another aspect of preferred embodiments, the implantable apparatus may further comprise a controller and controllable valves, wherein the controller operates the valves to control mixing of the liquid in the mixing chamber and delivery of the liquid through the catheter. Exemplary embodiments may further comprise sensors which detect a patient condition (e.g., hyperglycemia, arrhythmia), wherein the controller controls delivery of the liquid medication at least partially based on the sensed patient condition.

The implantable apparatus may also comprise an implantable bladder which may be configured to receive transcutaneous transfers of liquid. In some embodiments implantable bladder is be connected to the mixing chamber by an implantable tube. The bladder may be implanted in the patient along with the housing or it may be external to the patient with a fluid connection to the implantable apparatus housing and mixing chamber to facilitate the transfer of liquid into the mixing chamber. The mixing chamber within the implantable housing is configured to receive the liquid from the bladder and individual solid medication doses, wherein the individual solid medication dosages dissolve and/or become suspended in the liquid to form the liquid medication. In further aspects of the exemplary embodiments, the bladder has an access port through the external wall thereof to permit injection using a needle and syringe or other fluid delivery device.

The present invention also provides methods of use of the implantable drug delivery apparatus comprising implanting a housing having a mixing chamber and a catheter in the patient, wherein the housing carries a plurality of solid medication doses in an internal volume. An exemplary method further comprises transcutaneously delivering liquid to the mixing chamber and causing at least one solid medication dose to enter the mixing chamber wherein the solid medication dose dissolves or becomes suspended in the liquid to form the liquid medication. The method then further comprises delivering the liquid medication to a blood vessel via a catheter implanted between the mixing chamber and the blood vessel.

In preferred embodiments of the methods for delivering liquid medication to a patient transcutaneously delivering comprises injecting the liquid with a needle and syringe. However, other transcutaneous delivery means known in the art are also contemplated. In yet another preferred embodiment, the liquid is injected directly into the mixing chamber. Alternatively the liquid is injected directly into an implantable bladder and flows from the implantable bladder to the mixing chamber. In the mixing chamber the solid medication is dissolved or suspended in the liquid to form a liquid medication. The liquid medication is the pumped or directed to a catheter for delivery to a delivery site. In other contemplated embodiments the liquid medication is first directed to an intermediate chamber to be stored until it is needed. The liquid medication can then be directed or pumped to the delivery site.

In contemplated methods and apparatus described, wherein fluid is transcutaneously delivered to a bladder or mixing compartment, indicia may be made on the skin of the patient to aid in the direction and placement of the transcutaneous fluid delivery means. In a preferred embodiment wherein the fluid is delivered via needle and syringe a marker can be placed on the skin of the patient to direct the needle to the access port of the bladder or mixing chamber.

In preferred embodiments causing at least one solid medication dose to dissolve or become suspended in the liquid comprises mixing. In further embodiments delivering the liquid medication comprises pumping the liquid through the catheter.

The medication can comprise one or more drugs or other therapeutic agents for the treatment of various diseases and conditions. Many embodiments provide an implantable apparatus for delivering medication in liquid form to a target delivery site where the medication is stored in solid form (e.g., pellets, tablets, etc.) and mixed in a mixing compartment/reservoir with a liquid that is added to the mixing compartment via a skin access port (e.g., a resealable septum) using a syringe or other fluid delivery device. The reservoir and other components of the apparatus are disposed in an implantable housing which is configured to be implanted at any number of sites in the body. The housing includes at least one skin access port for adding fluid to the reservoir and another port to which a delivery member such as catheter is attached. The skin access port will typically comprise a re-sealable septum which is integral to the housing wall. Preferably, the housing is sized and shaped to be implanted near the skin surface to allow easy access by a syringe or other skin penetrating device to the skin access port. The reservoir also includes a re-sealable access port which may be one in the same as the skin access port. In one or more embodiments, the reservoir may comprise an expandable chamber such as a bellows which expands and becomes pressurized with the addition of fluid. The reservoir is coupled to an intermediary chamber (also referred to herein as a second reservoir) with a control valve separating the two. The pressure from the reservoir serves to drive fluid from the reservoir into the intermediary chamber. The intermediary chamber is, in turn, coupled to pumping means such as a micro-pump which is connected to a delivery catheter (or other delivery member) having a distal end positioned at the delivery site.

A store of solid form medication in the form of medication elements is located within the housing as well. The medication elements may correspond to pellets, tablets or other solid form medication known in the art. Each medication element may contain a therapeutically effective dose of one or more drugs. In some embodiments, the medication elements are contained in packaging containers, which in preferred embodiments, may correspond to foil wrapped containers which are hermetically sealed or otherwise have a low permeability to air and water vapor. In preferred embodiments, the store of solid form medication corresponds to a belt to which the medication elements or their packaging containers are attached. Typically, the belt will be positioned near or adjacent the exterior or the reservoir compartment and, in a preferred embodiment, surrounds at least a portion of the outer circumference of the reservoir. An advancement mechanism is operably coupled to the belt and is configured to advance a medication element from the belt through the re-sealable septum and into the reservoir. The advancement mechanism typically includes a drive means, such as a miniature electric motor and an advancement member, advanced by the drive means. The advancement member, which may correspond to a metal or polymer shaft, is configured to push on the medication element to detach it from the belt and/or push it out of its packaging container and through the re-sealable septum into the reservoir. Once in the reservoir, the medication element dissolves in fluid present or added to the reservoir (e.g. via the skin access port) to produce the medication solution.

A microprocessor or other controller can be used to allow for a fixed period of time after the medication element has been added to the solution to allow for sufficient mixing of the medication solution to produce a desired concentration of drug in the solution. Once sufficient mixing has occurred a control valve is opened to allow the medication solution to pass to the intermediary chamber. In some embodiments, the medication element can be configured to dissolve extremely rapidly (e.g., in seconds) so that a control valve need not be used. According to other embodiments, the apparatus need not include an intermediary chamber, so that micro-pump draws fluid directly from the reservoir. In such embodiments, a control valve can be used to control the flow of fluid from the reservoir to the micro-pump. Again, opening of the valve need not occur until adequate mixing/dissolving of the medication element has occurred using methods described herein.

In some embodiments, the reservoir may include a mixing element such as a magnetic stir bar or an impeller which mixes fluid within the reservoir to facilitate dissolving of the medication element in solution. Also, in some embodiments, the reservoir may include a sensor, to determine the concentration of drug in the medication solution and thus, whether sufficient dissolving of the medication element has occurred to produce the desired drug concentration in the medication solution. In one or more embodiments, the sensor may correspond to an optical sensor for measuring the optical density of the solution so as determine the drug concentration using optical density based techniques known the art (e.g., using Beer's Law). The reservoir may also include other sensors as well for determining the pressure and/or amount of fluid in the reservoir as described in more detail herein.

In some embodiments, the fluid or medication solution is transferred to from the mixing compartment to the intermediate chamber by pumping action. Alternatively, in various embodiments of the present invention fluid or medication solution is transferred from the mixing compartment the intermediate chamber by residual overpressure. The mixing compartment may feature an elastic (for instance elastic bellows or a balloon) construction that will elastically expand and contract. In this way, injecting fluid into the mixing chamber can over pressurize the mixing chamber. Actuation of a control valve upon proper mixing of the fluid and solid medication introduced therein will allow residual pressure from the elastic mixing chamber to transfer the medication solution to the intermediate chamber without the operation of a pump.

In some embodiments the fluid is transferred from a reservoir to the mixing compartment by pumping action. In embodiments further comprising a reservoir, the reservoir can also feature an elastic type construction that will allow elastic expansion and contraction of the reservoir. In this way, injecting fluid into the reservoir can over pressurize the reservoir. Actuation of a control valve will allow residual pressure from the reservoir to transfer the fluid to the mixing chamber without the operation of a pump.

The micro pump is configured to draw liquid from the intermediary chamber and pump it through the catheter to a target delivery site such as a vein, artery, organ or muscle. The micro-pump may be controllable via means of microprocessor or other controller described herein so as to control one or more of the amount and rate of delivery of medication solution to the delivery sites. Also, a control may separate the intermediary chamber and the micro-pump. In various embodiments, the micro-pump can be configured to deliver volumes of medication solution in a range from 1 µl to 100 ml. It may also be configured to detect for the presence of air bubble in solution so to stop and/or break down the bubble. It can also be programmed to periodically pump solution through the catheter to maintain the patency of the catheter or other delivery member.

One or more operations of the drug delivery device can be controlled by a controller such as a microprocessor. Such operations can include, for example, mixing in the mixing compartment, operation of the micro-pump and operation of one or more control valves connecting the mixing chamber to the intermediary chamber/reservoir and the intermediary chamber and the micro-pump. The apparatus can include one or more sensors to perform one or more of the following: i) detect when fluid has been added to the mixing chamber; ii) detect when the solution in the first reservoir has been mixed sufficiently to yield a desired drug concentration in the solution; iii) detect when the mixing chamber and/or intermediary chamber have run out of fluid; and iv) detect if the pressure in either reservoir has fallen below a specific threshold. In the latter two cases, the sensor can then send a signal to the controller to alert the user that more fluid needs to be added to the reservoir. The alert can be means of an audible alarm on the device and/or audible or other alarm (e.g., visual, tactile) on an external device such as a portable phone or other portable communication device to which the apparatus transmits an alarm signal.

In some applications, the delivery site (the site where the drug is delivered) can be the same as the target site (the site intended for the drug to reach and/or have a therapeutic or other effect on). In other applications, the target site can be different from the delivery site, for example, the delivery site can be intramuscular tissue in the chest and the target site can be the heart or the liver. The delivery site can be adjacent the target site, for example adipose tissue to deliver to underlying muscle tissue, or it can be placed at a non-oppositional site, for example, intramuscular delivery to reach the heart.

In various applications, embodiments of the invention can be used to deliver medication solution to provide treatment for a number of medical conditions including, for example, epileptic seizures, high blood pressure, elevated cholesterol, diabetes, coronary arrhythmia's (both atrial and ventricular), coronary ischemia (e.g., from a heart attack), cerebral ischemia, stroke, anemia or other like condition. The apparatus can be implanted at or near the target tissue or at remote delivery site (e.g., intramuscularly in the chest or thigh) with the catheter or other delivery member position near the target site or coupled to a vein to reach the target site by intravenous delivery.

In an exemplary embodiment of a method for using the invention, an embodiment of the apparatus can be implanted at a selected delivery site such as the arm, leg or hip. Desirably, the apparatus is implanted subcutaneously but near enough the skin surface so that the septum on the first reservoir is accessible by a needle syringe inserted through the skin to add saline or other fluid to the reservoir. Implantation can be done using an open or minimally invasive surgical procedure known in the art. Prior to implantation, the apparatus can be loaded with one or more belts or other medication described herein having a selected number of pellets (or other solid drug form of drug, e.g., tablets, etc.) to provide for delivery of pellets to the delivery site over an extended period of time, e.g., years. Once implanted, the pellets can be stored in the apparatus for an extended period of time (e.g., 1, 2, 5 years or longer) without degradation or deleterious effect to the pellets (e.g., loss of drug potency or therapeutic effectiveness). This is particularly the case when the pellets are stored in sealed packaging containers. The apparatus can programmed (e.g., via a controller such as a microprocessor or other logic resources known in the art) to deliver medication to the delivery site at regular intervals (e.g., once a day, week, month, etc.) or in response to an input from a sensor as is described herein. In the latter case, the input can be indicative of a particular medical condition (e.g., hyperglycemia) or an event such as an epileptic seizure or pre-seizure event. A controller described herein can be used to determine when to initiate delivery based on the sensor input and/or the time intervals for delivery for embodiments of the invention employing delivery at regular intervals. In either case, the controller can send a signal to the micro-pump other pumping means to deliver a dose of drug solution to the delivery site.

Embodiments of the invention can be used to provide concurrent treatment for two or more medical conditions eliminating the need for the patient to take multiple doses of multiple drugs (e.g., orally or by parenteral means) over the course of a day. This is particularly beneficial to patients who have long term chronic conditions (e.g., diabetes, Parkinson's disease, epilepsy, AIDS, cancer, etc) including those who have impaired cognitive abilities due to for example dementia or Alzheimer's disease. In use, such embodiments serve to improve patient compliance with one or more drug regimen's for the treatment of the condition and thus, clinical outcomes.

Further details of these and other embodiments and aspects of the invention are described more fully below, with reference to the attached drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Embodiments of the invention provide apparatus, systems, formulations and methods for delivering medication to various locations in the body. Many embodiments provide an implanted apparatus for delivering medication in liquid form wherein the medication includes one or more solid form drugs or other therapeutic agent for treating various medical conditions such as epilepsy, diabetes, high blood pressure, and high cholesterol. Particular embodiments provide an enclosed implanted apparatus for delivering medications/medication solutions to a delivery site DS and ultimately to a target tissue site TS (herein target site TS), such as the brain or heart, to treat a medical condition for an extended period of time.

Referring now to FIG. 1-4, an embodiment of an apparatus 10 for the delivery of a medication solution 101 to a delivery site DS, includes a housing 20, containing a first reservoir 30 (also referred to as mixing chamber 30), a second reservoir 40 (also referred to intermediary chamber 40), a pump means 50, a delivery member 60, a controller 70, power source 80, medication advancement mechanism 90 and a medication store 105 containing one or more solid form medication elements 100. One or more of reservoirs 30 and 40 and pump means 50 may be connected by connecting tubes 11 or other connecting means 11 which may correspond to polymer tubing known in the art. Also, one or more of reservoirs 30 and 40, pump means 50 and delivery member 60 may have controllable valves 54 positioned between them so to control the flow of fluid from an upstream chamber/device to that downstream. In particular embodiments, a control valve 55 can be placed between reservoirs 30 and 40 and another 56 between reservoir 40 and pump means 50 with other locations also contemplated. Control valve 54 may correspond to various miniature electronically controlled valves known in the art such as various miniature solenoid and reed valves.

Figure 1:
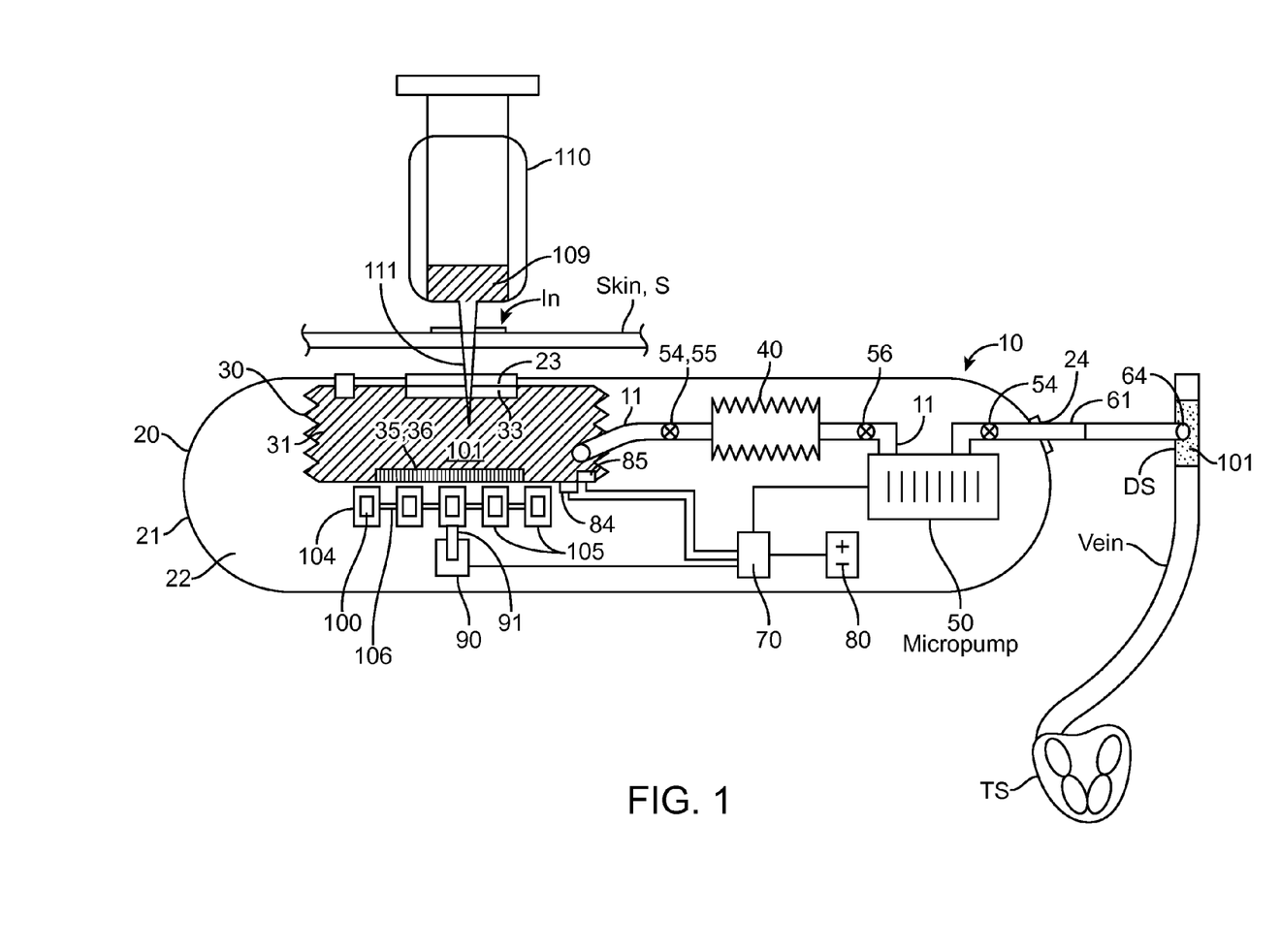
FIG. 1 illustrates an embodiment of a drug delivery apparatus including a first and second reservoir, micro pump and solid drug supply.

As is discussed herein, solid form drug elements 100 are configured to dissolve in water or an aqueous solution (e.g., saline) within reservoir 30 to form a medication solution 101. Elements 100 will typically comprise a drug 102 for the treatment of one or more conditions (e.g., epilepsy, arrhythmia, diabetes, etc.) and one or more excipients 103 such as disintegrants, preservatives, binders etc. In preferred embodiments, excipients 103 include disintegrants known in the art to facilitate the dissolving of the element in water and/or saline or other aqueous solution used in the pharmaceutical arts. Elements 100 may have a shape corresponding one or more of pellets, tablets, caplets, cylinders and other solid forms known in the pharmaceutical arts. For ease of discussion, they will now be referred to as medication pellets 100 or pellets 100, but all other forms described herein are equally applicable. According to one or more embodiments, pellets 100 may be stored in hermetically sealed puncturable packaging containers as discussed herein.

Housing 20 is configured to be implanted beneath the skin S and includes one or more sealable port 23 for penetration by the needle 111 of a needle syringe 110 or other tissue penetrating element 111. Sealable port 23 will typically comprise a sealable septum 23 fabricated from various elastomeric materials (e.g., silicone, polyurethane). In some embodiments, sealable septum 23 may be one in the same or otherwise contiguous with sealable septum 33 on reservoir 30. Indica In is shown on the patients skin. Indicia In serves to aid in the direction and placement of needle 111. Housing 20 may also include an opening 24 for attachment of catheter or other delivery member 60. It can be sized and otherwise shaped to be placed in one or more locations within the patient's body, including, for example, locations within one or more of patients, arms, legs, torso or pectorial region. Further, it may be sized and otherwise structured to be positioned in both supermuscular and intramuscular sites, later examples including the patient's biceps, triceps or thigh muscles. Typically, it will have a cylindrical shape with rounded ends but other shapes are also contemplated. It may be fabricated from biocompatible metals and/or polymers and has a tissue contacting surface 21 and an interior space 22. Tissue contacting surface 21 may comprise various biocompatible polymers and/or polymer coatings known in the art including for example, silicone, polyurethanes and polytetrafluoroethylene (PTFE).

In various embodiments, all or portions of housing 20 can also be constructed from conformable materials (e.g., polyurethane silicone and other elastomeric polymers) to conform to the shape of surrounding tissue layers and or shape of the tissue compartment in which it is placed, e.g., the contour of the bladder, vagina, gall bladder, etc., or the contour of the skin overlying the implantation site. Conforming materials can also be employed to allow for surrounding body tissue to grow around and reshape the housing during prolonged periods of implantation. In this way, embodiments having a flexible housing minimize the effect of the housing on the growth and function of surrounding tissue, thus allowing the apparatus to be implanted over very prolonged periods including allowing the apparatus to be implanted in children and remain through adulthood. Various conformable materials can also be used to facilitate implantation of apparatus 10 using minimally invasive methods. Such materials allow the apparatus including housing 20 to bend, twist or otherwise conform so as to be inserted through surgical ports and guiding devices and then reassume its shape once positioned at the intended implantation site. In particular embodiments, bending and twisting of housing 20 can be further facilitated by the use of flexible joints built into the housing. Housing 20 can also be sized and shaped to further facilitate implantation using minimally invasive surgical methods. For example, the housing can have a particular size and shape such as a cylindrical shape to enable it pass through various minimally invasive surgical ports and guiding devices. The housing may also be configured to have a collapsed non-deployed state and an expanded deployed state where the non-deployed state is used for advancing the housing and the deployed state once the housing is positioned at a desired location in the body.

In one or more embodiments, the first reservoir 30 may correspond to an expandable device such as an expandable bellows which expands and becomes pressurized with the addition of fluid 109 from syringe or other fluid delivery device 100. Other expandable devices are also contemplated such as expandable balloon. The reservoir 30 includes a re-sealable septum 33 for access by syringe 110 so as to inject saline or other fluid 109 from the syringe or other fluid deliver device 110 (e.g., a pump, etc.). Septum 33 may comprise various sealable elastomers such as silicone or polyurethane. In some embodiments, septum 33 is one in the same or otherwise contiguous with septum 23 on housing 20. For example, in particular embodiments, septum 33 can be placed directly below septum 23 and may be attached to it. Reservoir 30 also may include another re-sealable septum or port 35 (described in further detail herein) configured to allow insertion of pellets or other solid medication element 100 by advancement mechanism 90 into the reservoir. Pellet 100 may be inserted into the reservoir before or after the addition of fluid to the reservoir by syringe 110 or other fluid delivery means. In either case, the pellet is configured to dissolve to form a medication solution 101. Once filed with solution, reservoir 30 has an internal pressure which is then used to supply fluid to second reservoir 40, which may also correspond to an expandable bellows but of a smaller size than reservoir 30. Filling of reservoir 40 with fluid from reservoir 30 can be controlled by a control valve 55 which according to one or more embodiments, may be controllable by controller 70 or other control means (e.g., an external controller). Reservoir 40 is in turn coupled to pumping means 50 such as a micro-pump 50 which is connected to a delivery catheter 60 having a distal end 61 positioned at the delivery site DS.

A store 105 of solid form drug 100 is coupled to a side of reservoir 30 and can be inserted through a re-sealable wall or port of reservoir 30 via a delivery mechanism 90. The micro pump 50 is configured to draw liquid from reservoir 40 and pump it through the catheter 60 to a target delivery site DS such as a vein, organ or muscle. The micro-pump 50 can also be configured to deliver selectable doses of drug solution 101 in the microliter or milliliter range. Other ranges are also contemplated.

In various embodiments, one or more operations of the drug delivery apparatus 10 can be controlled by a controller 70. Controller 70 may correspond to a microprocessor or other logic resources known in the art (e.g., a state device, analogue device, etc.) and also may include memory resources such as RAM, DRAM, ROM, etc. The logic resources and/or memory resources may include one or more software modules for operation of the controller. Through the use of modules, the controller 70 may be programmed to include a medication delivery regimen wherein medication/medication solution is delivered at regular intervals (e.g., once or twice a day, etc.) over an extended period. The controller 70 may also include an RF device for receiving a wireless signal (e.g., wireless or otherwise) to initiate the delivery of medication or to change the delivery regimen (e.g., from once a day to twice a day). In this way, the patient or a medical care provider can control the delivery of medication in response to a specific event (e.g., an episode of angina) or longer term changes in the patient's condition or diagnosis.

The operations of apparatus 10 which can be controlled by controller 70 can include, for example, mixing in the mixing reservoir 30, operation of the micro-pump 50, operation of one or more control valves 54 (e.g., valves 55, 56 and 57) and actuation and control of pellet advancement mechanism 90. Such operations can be facilitated by the use of one or more sensors 84. According to various embodiments, sensors 84 can be configured to perform one or more of the following functions: i) detect when fluid has been added to the mixing chamber; ii) detect when the 101 has been mixed sufficiently to yield a desired drug concentration in the solution; iii) detect when the amount of fluid in the mixing chamber and/or intermediary chamber has fallen below a set threshold; and iv) detect if the pressure in either reservoir has fallen below a set threshold. In all fours cases, the latter two in particular, the apparatus (e.g., through use of controller 70) can be configured to alert the user of such condition via an audible/tactile alarm from the apparatus and/or via an audible, tactile or other alarm from a portable phone or other portable device to which the apparatus transmits an alarm signal. Also in various embodiments, the controller 70 can be programmed to include a delivery regimen wherein medication is delivered at a selected regular intervals (e.g., once or twice a day, etc.) over an extended period. It can also be configured to receive a signal (e.g., wireless or otherwise) to initiate the delivery of medication or to change the delivery regimen (e.g., from once a day to twice a day). In this way, the patient or a medical care provider can titrate the delivery of medication in response to a specific event (e.g., an episode of angina, an epileptic seizure, etc.) or to longer term changes in the patient's condition or diagnosis (e.g., increased insulin tolerance).

Figure 1A:
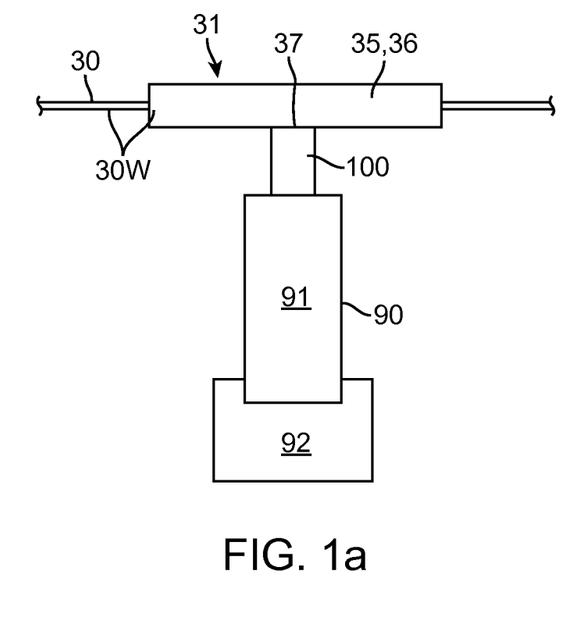
FIGS. 1a and 1b illustrate an embodiment of a resealable septum for delivery of solid drug into the first reservoir.
Figure 1B:
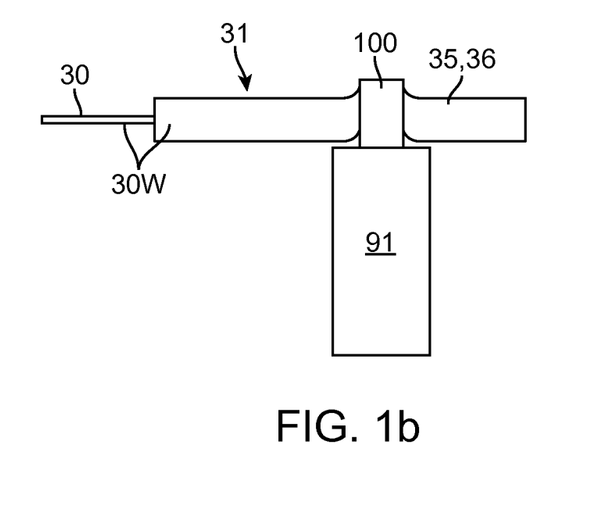
Figure 1C:
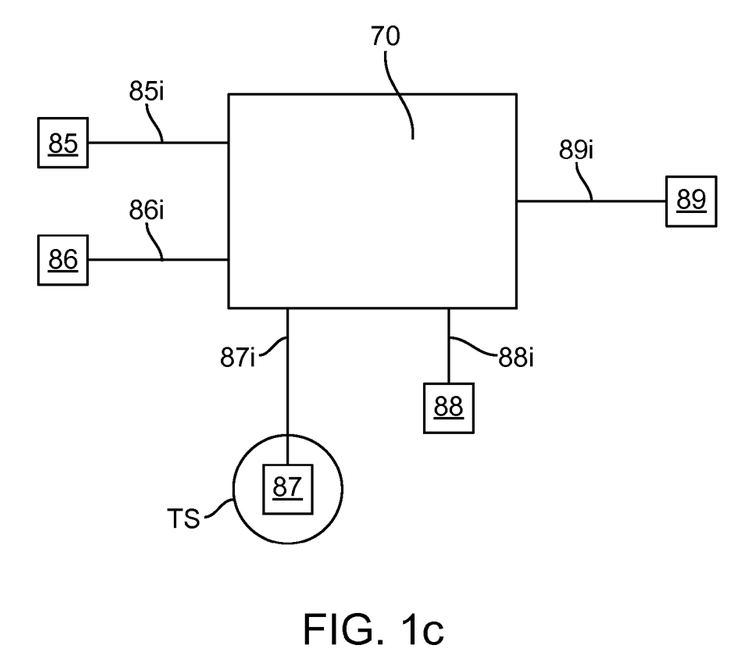
FIG. 1c is a block diagram illustrating various sensors which may be with used embodiments of the drug delivery apparatus.

According to one or more embodiments, the controller 70 can operably coupled to and receive inputs from one or more of sensors 84, including for example sensors one or more of sensors 85, 86, 87, 88 and 89 is shown in the embodiment of FIG. 1c. In one embodiment, the controller is coupled to a sensor 85 positioned within reservoir 30 so as to receive an input 85i indicative of the pressure and/or fluid amount present within the reservoir. As described herein, such an input 85i can be used to alert the user/patient when the fluid level or pressure within reservoir 30 falls below a set threshold within the reservoir. Sensor 85 may correspond to one or more of a pressure sensor (e.g., solid state strain gauge) or fluid volume sensor known in the art.

In another embodiment controller is operably coupled to a sensor 86 which senses a physiologic parameter indicative of a condition to be treated by the drug in the medication pellet, for example, a glucose sensor to sense diabetic hyperglycemia (which can be treated by insulin or analogue or derivative thereof). When controller 70 receives an input 86i from sensor 86 indicative of the condition, it initiates actuation of the micro-pump or other pumping means 40 to deliver a dose of medication solution 101. Both the initial and subsequent inputs from the sensor 86 can be used to titrate the delivery of medication solution over an extended period until the condition is dissipated or otherwise treated. Sensor 86 is typically implanted, such as in the case of glucose sensor, though not necessarily. In some cases, the sensor 86 may be worn or carried by the patient such as a sensor for the measurement of pulse rate and/or $Po_2$ levels and transmits its inputs 86i to controller 70 via an Rf signal or other transmission means.

The controller 70 can also receive inputs 87i from other sensors 87 configured to measure the blood or other tissue concentration of the delivered drug. These inputs can also be used to titrate the delivery of the medication solution 101 to achieve a selected concentration of drug (e.g., in plasma, tissue, etc.) well as a selected pharmacokinetic profile (e.g., $c_{max}$, $t_{max}$ $t_{1/2}$, etc.). The drug sensors 87 can be positioned at the target tissue site TS as well as other sites in the body (e.g., a vein or artery) in order to develop a pharmacokinetic model of the distribution of the drug at multiple sites in the body.

The apparatus can also include a sensor coupled to the controller 70 which indicates how much solution 101 is left in the first reservoir 30 and/or how many medication pellets 100 are left in store 105. The controller in turn, can signal this information to an external communication device such as a cell phone, portable monitor or remote monitor (e.g., at the physician's office). In this way, the patient and/or medical care provider can take appropriate action well before the apparatus runs out of medication pellets 100 and/or medication solution 101.

Figure 2:
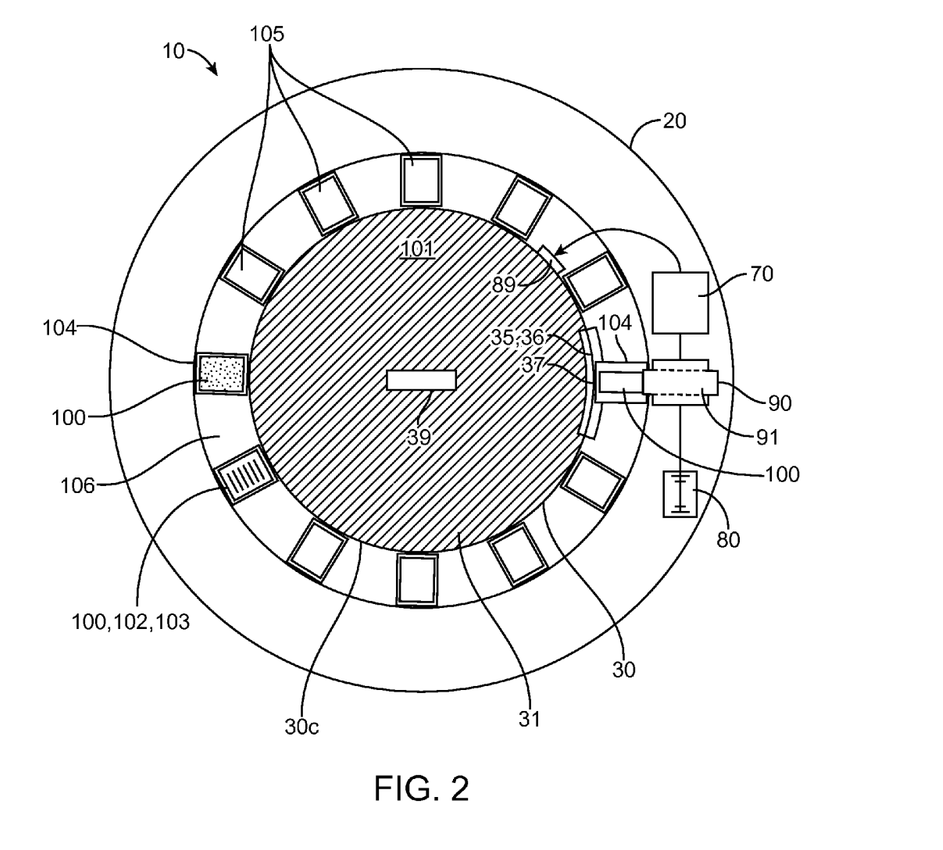
FIG. 2 illustrates an embodiment of a solid drug belt and advancement means for advancing solid drug pellets into the first reservoir.

According to one or more embodiments, medication store 105 corresponds to one or more belts 106 having a plurality of attached medication pellets 100 or attached packaging containers 104 containing the pellets. Belt 106 can comprise a polymer film or metal foil or other thin film material. Containers 101 can be attached to belt 106 along a surface of the packaging container body or they may be centrally attached or otherwise integral to belt 106. Such embodiments can be achieved by fabricating belt 106 and containers 104 from the same strip or other piece of material (e.g., polymer film, metal foil, etc.). Containers 104 may be attached to belt 106 using various attachment methods known in the art including adhesive bonding, ultrasonic welding, RF welding and others. In various embodiments, packaging containers 104 can comprise various sealable foils and polymers known in the pharmaceutical packaging arts, for example, PET, HDPE and other materials known in the art. In some embodiments, container 104 may have a two-ply construction for improved impermeability.

Figure 2A:
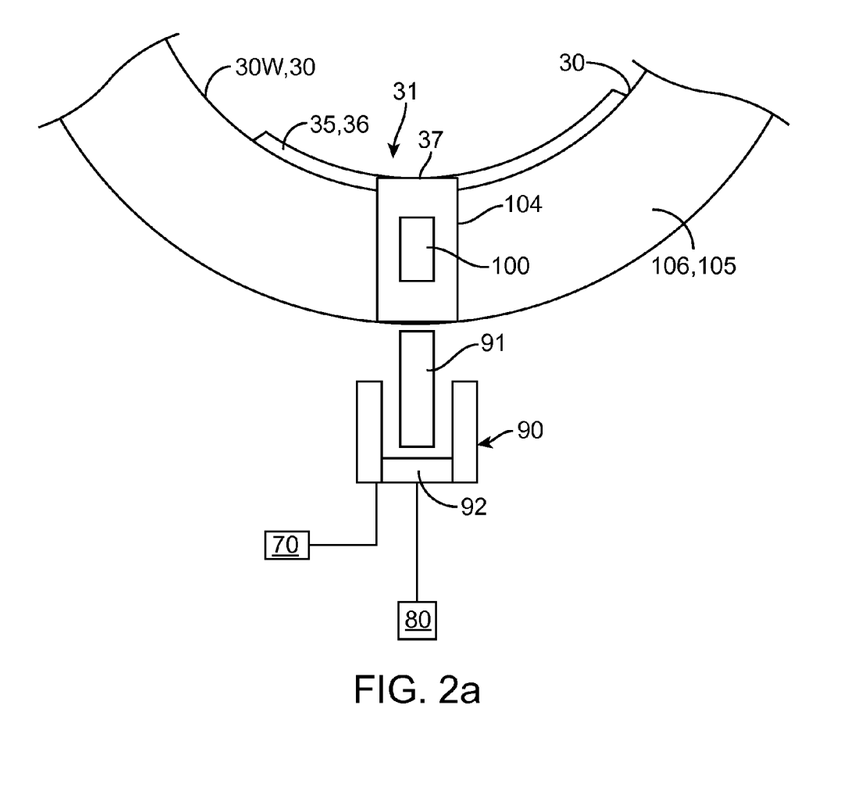
FIG. 2a illustrates an embodiment an embodiment of an advancement mechanism for advancing solid drug pellets into the first reservoir.

In many embodiments, belt 106 surrounds the outer surface of the reservoir 30. In a preferred embodiment belt shown in FIG. 2, belt 106 surrounds the outer circumference 30c of an embodiment of reservoir 30 having a cylindrical or cylindrical capsule shape (i.e., approximately a hot dog shape). As discussed herein, a delivery mechanism 90 is included for engaging the belt 106 and transferring an individual medication pellet 100 from the belt through a sealable septum 36 of the reservoir wall 30w and/or other sealable port 35 in the reservoir and into reservoir interior 31. There, the medication pellet is dissolved in fluid 109 present within or added to reservoir 30. In many embodiments, the delivery mechanism comprises an advancement member 91 and advancement means 92 as is shown in the embodiments of FIGS. 2 and 2a. For embodiments having pellets 100 (or other solid form medication 100) stored in a packaging container 104, the advancement member 91 may also be configured to puncture the packaging container and push the pellet from the container and into the reservoir through the reservoir port or sealable portion of the reservoir. The delivery mechanism 90 is also desirably configured to advance the belt 106 so as to as to bring another packaging container in alignment with the advancement member for delivery of the next pellet into the reservoir. This can be accomplished by indexing the belt. Advancement mean 92 will typically be powered by power source 80 (e.g., an electrochemical battery) but in some embodiments, may have its own separate power source.

In many embodiments, delivery member 60 corresponds to a flexible catheter 60 that is coupled to an opening 24 or other opening in housing 20. Catheter 60 has a length selected to deliver medication solution 101 to selected delivery site DS. The inner diameter of the catheter 60 can be selected to allow the medication solution to flow through the catheter without significant fluid resistance. Catheter 60 can be fabricated from one or more biocompatible polymers known in the art such as PeBax, silicone, polyethylene polyurethane, etc. Desirably, the distal tip 62 of the catheter has an atraumatic configuration to allow for extended periods of implantation at the target delivery site DS without a foreign body response such as inflammation, etc. The catheter 60 including tip 62 as well other portions of apparatus 10 can also include antibacterial coatings such as various antibiotics and silver coating to minimize bacterial adherence and/or infection. Such coating can also be used in other portions of apparatus 10 as well including one or more of housing 20, reservoirs 30 and 40 and pump 50. In some embodiments, apparatus 10 can include multiple catheters 60 so as to allow for the delivery of medication solution to multiple delivery sites using a single delivery apparatus 10. For example, in one embodiment, apparatus 10 may include a first catheter 60 positioned in a vein and second catheter 60 positioned in an intramuscular site. In use, such embodiments provide for varying rates of delivery and associated pharmacokinetics for a particular drug. For example, systemic delivery can provide for achieving a rapid increase in the blood concentration (e.g., a shorter $t_{max}$) of the drug but a smaller t ½, while an intramuscular delivery can be use to achieve a slower rate of delivery (a longer t max) but with longer term delivery of drug (e.g., a larger t ½)

Figure 3:
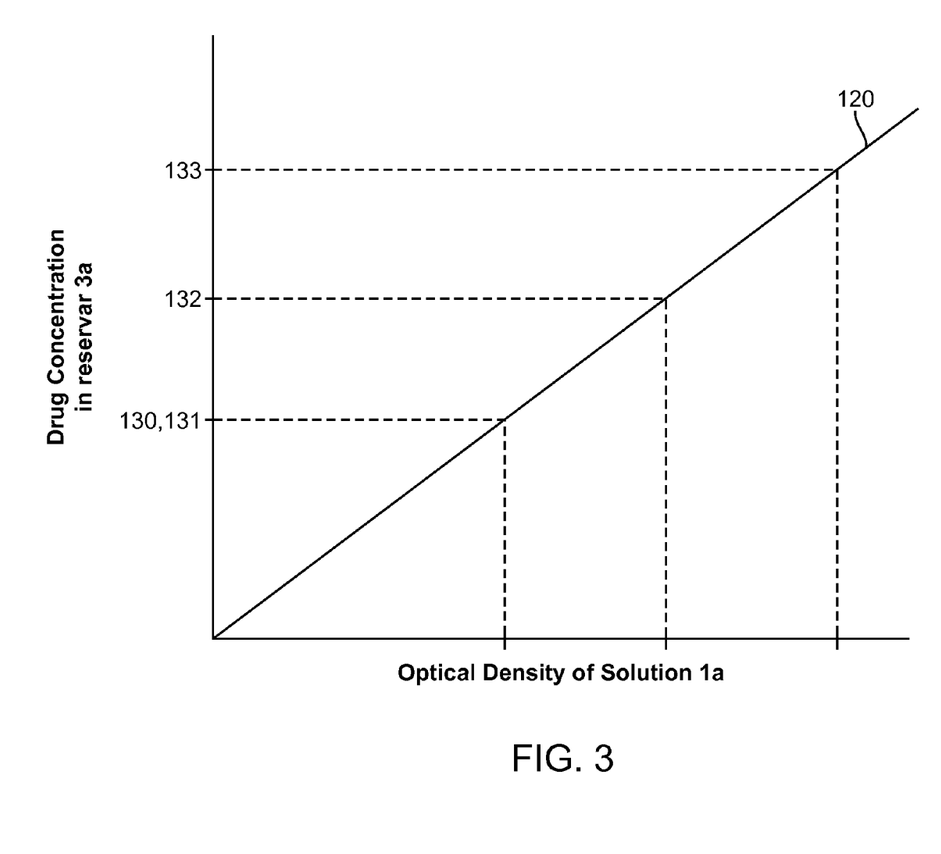
FIG. 3 illustrates a graph of drug concentration versus optical density which can be used for ascertaining the level of mixing of drug in the mixing chamber reservoir.

Desirably, pellets 100 are configured to rapidly dissolve in liquid 109 to produce a medication solution 101 having a desired concentration of drug in the solution. To permit sufficient time for such dissolving, controller 70 can be configured to keep the control valve 55 between reservoir 30 and 40 closed for a set time period determined to be sufficient for dissolving of pellet 100. In some embodiments, dissolving of pellets 100 in solution 109 can be facilitated by use of mixing means such as mixing elements 39 as is described below. In other embodiments, dissolving can be facilitated by heating elements (not shown) and/or the use of the patients body heat (in the latter case one or more of the housing and or reservoir 30 can be made of thermally conductive materials to conduct heat from the patient into the reservoir). Also, in various embodiments, the mixing of solution 101 and/or the time for dissolving of medication 100 in fluid 109 can be controlled, for example, by the use of one more sensors 84. In particular embodiments such a sensor can correspond to a sensor 89 selected determine the concentration of drug in the medication solution 101 and thus, whether sufficient dissolving of the medication pellet 100 has occurred to produce the desired drug concentration in the medication solution 101. In one or more embodiments, the sensor 89 may correspond to an optical sensor for measuring the optical density of solution 101 so as determine the drug concentration using optical density based techniques known the art (e.g., using Beer's Law). Sensor 89 can be on the outer surface of reservoir 30 (as is shown in FIG. 2) or in the interior 31 and can be operably coupled to controller 70 so as to send an input 89i to the controller indicative of the optical density in solution 101. As shown in FIG. 3, a mathematical correlation 120 between optical density and drug concentration in solution 101 can be established using such techniques. Further, using such a correlation 120, thresholds 130 can determined for the minimum 131, optimal 132 and high 132 levels of drug concentration in solution 101. According to one embodiment, controller 70 (or other control means) allows the dissolving process to continue to at least the minimum threshold 131 and more desirably to the optimal threshold 132. When such thresholds have been reached, the controller then allows the solution 101 to be passed on from the reservoir 30 to reservoir 40 via control of valve 55. The controller may send a signal to the user (e.g., via a portable device such as a cell phone) indicating this has occurred as well. Also, if for some reason, the concentration of drug in the reservoir exceeds threshold 133, the controller may send a send a signal to the user (via the portable device or other communication means) to add a specific amount of fluid to reservoir 30 so as to bring down the concentration of fluid. In the meantime, the controller may cease further delivery of solution 101 to reservoir 40 and or micro-pump 50. For embodiments of apparatus 10 including a fluid bladder 45, the controller may also send a signal to a control valve 57 connecting the bladder 45 to the reservoir to receive more fluid from the bladder. In such embodiments the fluid can pulled in via means of the pressure in the bladder or a pump fluidically (not shown) coupling bladder 45 and reservoir 30.

According to one or more embodiments, dissolving of pellets 100 can be facilitated by the use of one or more mixing elements 39 placed in reservoir 30. According to one or more embodiments, the mixing elements 39 may correspond to various magnetic stir bars (desirably coated with an inert material) which may be powered magnetic fields generated by embodiments of advancement means 92 comprising a rotary electromagnetic motor. According to other embodiments, mixing elements 39 may correspond to an impeller operably coupled to advancement means 92 and/or mechanism 90. In either case, controller 70 can be configured to initiate mixing of fluid 109 once fluid 109 and pellet 100 have been added to the reservoir. Detection of the presence of fluid 109 within the reservoir 30 (or 40) can be achieved by the use of one or more sensors 84 which may be positioned in or otherwise fluidically coupled to the reservoir 30 or 40 as the case may be. Also inputs from sensors 89 can be used to control mixing elements 39.

Power source 80 may correspond to various miniature electrochemical batteries known in the art such as a lithium, lithium ion or other storage battery and may be coupled to one or more of controller 70, pump means 50, control valves 54 and advancement mechanism 90. It may also configured to be rechargeable by conductive coupling to a charging source known in the art positioned above the area of skin S below which apparatus 10 is implanted.

In many embodiments, port 35 comprises a sealable septum 36 allowing a solid dose of medication 100 to be passed through the septum by mechanism 90 without the ingress of fluids into housing interior 31 as is shown in the embodiment of FIG. 1. Septum 36 can comprise various elastomeric polymers known in the art such as silicone or polyurethane which are configured to sufficient resilience to open and then seal on itself after being punctured or otherwise opened by the passage of medication pellet 100. In particular embodiments, septum 36 can have a re-sealable slit 37, that is normally in a closed and is opened by the passage of medication 100 only to close again on itself after medication 100 passes through due to the elasticity and resilience of the material making up septum 36 as is shown in the embodiments of FIGS. 1a and 1b.

Figure 4:
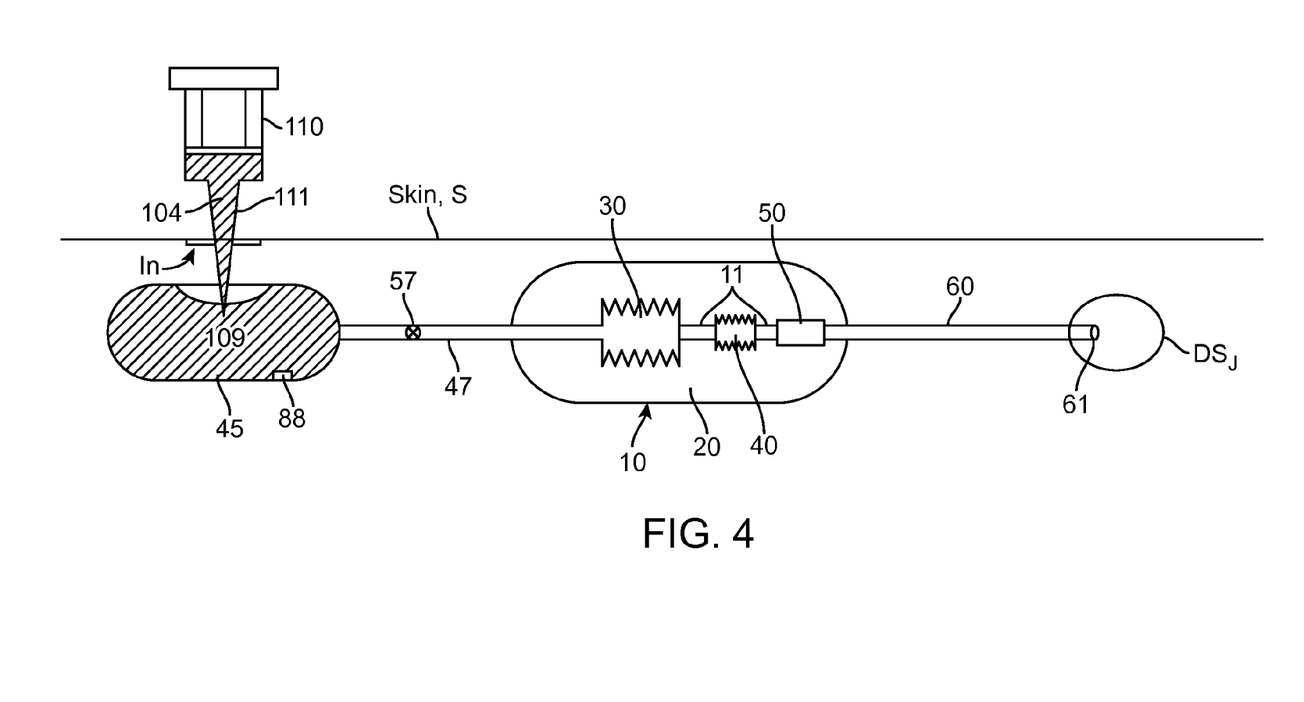
FIG. 4 illustrates an embodiment of a drug delivery apparatus including a reservoir coupled to a fluid bladder for filling the reservoir, a micro pump, catheter and solid drug supply.

In additional or alternative embodiments, fluid 109 may be added to reservoir 30 by means of a bladder 45 that is fluidically coupled to reservoir 30 by means of a connecting tube or other fluid coupling means 47 as is shown in the embodiment of FIG. 4. A control valve 57 (which may be controlled by controller 70 or other control means) may also be positioned between bladder 45 and reservoir 30 to control the flow of fluid 109 from bladder to the reservoir 70. Similar to reservoir 30 bladder, 45 can be configured to be pressurized by the injection of fluid 109 such that that pressure is sufficient to provide the driving force for fluid flow between bladder 45 and reservoir 30. Alternatively, a pump or other pumping means (not shown) may be fluidically coupled to bladder 45 and reservoir 30 to pump fluid from the bladder to the reservoir. Use of such a secondary pump may be controlled by controller 70 or other control means.

Typically, bladder 45 is configured to be implanted (e.g., subcutaneously) as is shown in embodiment of FIG. 4. However, in other embodiments, bladder 45 may be positioned external to the patient's body with the connecting tube or other fluid coupling means 47 passing through the patient's skin. In such embodiments, the bladder 45 may be configured to be worn or otherwise carried by the patient. For implanted embodiments, bladder 45 will typically include a re-sealable septum 46 or other re-sealable port 46 similar to septum 23 for subcutaneous injection of fluid 109 by a syringe or other fluid delivery means 110. Non implanted embodiments of bladder 45 may also include such a septum 46.

The fluid 109 from bladder 45 may be used to pressurize the reservoir and/or form a medication solution 101 with pellet 100 or other solid form drug 100. Such fluid may comprise water, saline or other aqueous solution for mixing with pellet 100 in reservoir 30. Bladder 45 may be fabricated from various liquid water/gas impermeable biocompatible polymers known in the art an example of which includes isobutyl rubber and one or more co-polymers thereof. It may have a volume in the range of 5 to 300 ml, though other volumes are contemplated. Bladder 45 may also include one or more sensors 88 to sense one or more of the pressure and amount of fluid 109 in bladder 45. Such sensors can include various pressure, optical and/or impedance sensors known in the art. Similar to use of sensors 85 within reservoir 30, sensors 88 may be used by controller 70 to send an alert the patient, when one or more of the volume or pressure within bladder 45 has fallen below a threshold level.

Desirably, store 105 including belt 106 contains a sufficient supply of medication pellets 100 to provide treatment of a particular medical condition for an extended period of time, for example, two to five years or longer. In various embodiments, belt 106 can hold up to several hundred or more pellets 100. In various embodiments, apparatus 10 can include multiple belts 106, including two, three or more belts which may surround all or a portion of bellows reservoir 30. In these and related embodiments, apparatus 10 can include means for switching over from a first to a second belt 106. Such switching means (not shown but readily comprehendible to those skilled in the electro-mechanical arts) can include for example, a solenoid and can be stand alone or incorporated into pellet advancement mechanism 90 (Also referred to as advancement mechanism).

A discussion will now be presented of delivery mechanism 90 (also referred to sometimes as advancement mechanism 90), herein mechanism 90. In many embodiments, mechanism 90 comprises an advancement member 91 coupled to advancement means 92 which may correspond to a miniature electric motor, including a linear induction motor. Advancement means 92 may also correspond to a piezo-electric device which is configured to deform and move in response to an applied voltage, for example from controller 70 and/or power source 80. In various embodiments, advancement member 91 corresponds to a wire or plastic shaft configured to have sufficient column strength to advance pellet 100 through septum 36 and into reservoir 30. For embodiments where pellet 100 is contained in packaging container 104, advancement member 91 is also configured (e.g., via column strength etc.) to puncture the packaging container and push pellet 100 out of the container and through septum 36. This may include configuring advancement member 91 to have a tapered or pointed tip for puncturing packaging container 104.

In alternative or additional embodiments, belt 106 can include a separate belt drive mechanism (not shown) which may correspond to a sprocket, gear, etc. or other engageable advancement means configured to be driven by mechanism 90. The separate drive mechanism may be directly coupled to mechanism 90 (e.g., via a gear or other mechanical linkage) or may be indirectly coupled to it via means of controller 70 which sends signals to the separate drive mechanism in response to an input or signals sent to mechanism 90.

In an exemplary embodiment of a method for using the invention, an embodiment of apparatus 10 can be implanted at or near a selected delivery site DS such as the arm, leg hip or a blood vessel. For embodiments where the delivery site DS is a blood vessel (e.g., a vein or artery), the apparatus is implanted in tissue near the selected blood vessel and then, the distal end 62 or larger distal portion of catheter 60 is positioned in the blood vessel. Desirably, the apparatus is implanted subcutaneously but near enough the skin surface S so that the septum 23 on the first reservoir 30 is accessible by a needle 111 of syringe 110 (or other fluid delivery device) inserted through the skin to add saline or other fluid to the reservoir. Indicia In may be used to aid in the placement and direction of needle 111. Implantation can be done using an open or minimally invasive surgical procedure known in the art. Prior to implantation, apparatus 10 can be loaded with one or more belts 106 (or other drug store 105) having a selected number of pellets (or other solid drug form medication) to provide for delivery of pellets to the delivery site over an extended period of time, e.g., years. Once implanted, the pellets can be stored in the apparatus for an extended period of time (e.g., 1, 2, 5 years or longer) without degradation or deleterious effect to the pellets (e.g., loss of drug potency or therapeutic effectiveness). The apparatus can programmed (e.g., via a controller 70) to deliver medication/medication solution to the delivery site at regular intervals (e.g., once a day, week, month, etc.) or in response to an input 86i from one or more sensors 86, such as a glucose sensor. In the latter case, the input can be indicative of a particular medical condition (e.g., hyperglycemia) or event such as an epileptic seizure or pre-seizure event. Controller 70 can be configured to determine when to initiate delivery based on the input of sensor 86 (or other sensor) and/or the time intervals for delivery for embodiments of the invention employing delivery of medication at regular intervals. In either case, the controller can send a signal to micro-pump 50 other pumping means to deliver one or more doses of drug solution 101 to the delivery site DS or sites.

Conclusion

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the apparatus can be sized and otherwise adapted for various pediatric and neonatal applications. Also, various embodiments of then invention can be sized and otherwise adapted for various veterinary applications, including for example, animals such one or more of bovine, equine, porcine, canine, feline. In such cases, embodiments of the invention can be used for the delivery of various antibiotics, antivirals and other agents for treatment or prevention of various diseases common to domesticated animals.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand-alone elements. Hence, the scope of the present invention is not limited to the specifics of the described embodiments, but is instead limited solely by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An implantable apparatus for delivering a liquid medication to a delivery site in a patient, said apparatus comprising:
   an implantable housing having an external wall and an internal space;
   a mixing chamber within the internal space, wherein the mixing chamber is configured to receive transcutaneous transfers of a liquid;
   a plurality of solid medication doses in the internal space;
   wherein said mixing chamber is configured to receive individual solid medication doses from the internal space, and wherein the individual solid medication dosages dissolve or become suspended in the liquid within the mixing chamber to form the liquid medication;
   a transfer mechanism for advancing individual solid medication doses from the internal space into the mixing chamber, wherein the mechanism advances the individual solid medication dose through a split membrane in a side of the mixing chamber and wherein the individual solid medication doses are carried in a carousel which is incremented to move individual doses adjacent the split membrane; and
   a catheter configured to receive the liquid medication from the mixing chamber and to deliver the liquid medication to the delivery site.

2. An implantable apparatus as in claim 1, wherein the mixing chamber has an access port through the external wall of the housing to permit injection using a needle and syringe.

3. An implantable apparatus as in claim 1, further comprising a pump for delivering liquid medication doses through the catheter.

4. An implantable apparatus as in claim 1, further comprising a controller and controllable valves, wherein the controller operates the valves to control mixing of the liquid in the mixing chamber and delivery of the liquid through the catheter.

5. An implantable apparatus as in claim 4, further comprising sensors which detect a patient condition, wherein the controller controls the delivery of the liquid medication at least partially based on the sensed patient condition.

6. An implantable apparatus as in claim 1, further comprising an intermediate chamber between the mixing chamber and the catheter.

7. An implantable apparatus as in claim 1, wherein the delivery site is a blood vessel and a distal portion of the catheter is configured to be placed in the blood vessel.

8. An implantable apparatus for delivering a liquid medication to a blood vessel of a patient, said apparatus comprising:
- an implantable housing having an external wall and an internal space;
- an implantable reservoir configured to receive transcutaneous transfers of a liquid;
- a plurality of solid medication doses in the internal space;
- a mixing chamber within the implantable housing, said mixing chamber configured to receive liquid from the reservoir and individual solid medication dosages, wherein the individual solid medication dosages dissolve in the liquid in the mixing chamber to form the liquid medication;
- a transfer mechanism for advancing individual solid medication doses from the internal space into the mixing chamber, wherein the mechanism advances the individual solid medication dose through a split membrane in a side of the mixing chamber and wherein the individual solid medication doses are carried in a carousel which is incremented to move individual doses adjacent the split membrane; and
- a catheter configured to receive the liquid medication from the mixing chamber and to deliver the liquid medication to the blood vessel.

9. An implantable apparatus as in claim 8, wherein the implantable reservoir is connected to the mixing chamber by an implantable tube.

10. An implantable apparatus as in claim 8, wherein the reservoir has an access port through the external wall thereof to permit injection using a needle and syringe.

11. An implantable apparatus as in claim 8, further comprising a pump for delivering liquid medication doses through the catheter.

12. An implantable apparatus as in claim 8, further comprising a controller and controllable valves, wherein the controller operates the valves to control mixing of the liquid medication in the mixing chamber and delivery of the liquid medication through the catheter.

13. An implantable apparatus as in claim 12, further comprising sensors which detect a patient condition, wherein the controller controls the delivery of the liquid medication at least partially based in the sensed patient condition.

14. An implantable apparatus as in claim 8, further comprising an intermediate chamber between the mixing chamber and the catheter.

15. An implantable apparatus for delivering a liquid medication to a delivery site in a patient, said apparatus comprising:
- an implantable housing having an external wall and an internal space;
- a mixing chamber within the internal space, wherein the mixing chamber is configured to receive transcutaneous transfers of a liquid;
- a plurality of solid medication doses in the internal space;
- wherein said mixing chamber is configured to receive individual solid medication doses from the internal space, and wherein the individual solid medication dosages dissolve or become suspended in the liquid within the mixing chamber to form the liquid medication;
- a transfer mechanism for advancing individual solid medication doses from the internal space into the mixing chamber, wherein the mechanism advances the individual solid medication dose through an resealable septum in a side of the mixing chamber and wherein the individual solid medication doses are carried in a carousel which is configured to move individual doses adjacent the resealable septum; and
- a catheter configured to receive the liquid medication from the mixing chamber and to deliver the liquid medication to the delivery site.

* * * * *